United States Patent [19]

Plapp

[11] 4,341,114

[45] Jul. 27, 1982

[54] APPARATUS FOR BURNOFF OF A RESISTOR, IN PARTICULAR OF A HOT WIRE IN AN AIR FLOW RATE METER OF AN INTERNAL COMBUSTION ENGINE

[75] Inventor: Günther Plapp, Filderstadt, Fed. Rep. of Germany

[73] Assignee: Robert Bosch GmbH, Stuttgart, Fed. Rep. of Germany

[21] Appl. No.: 154,688

[22] Filed: May 30, 1980

[30] Foreign Application Priority Data

Jul. 20, 1979 [DE] Fed. Rep. of Germany ....... 2929434

[51] Int. Cl.³ .......................................... G01M 15/00
[52] U.S. Cl. ....................................... 73/118; 73/204
[58] Field of Search ......................... 73/118, 204, 116

[56] References Cited

U.S. PATENT DOCUMENTS 4,196,622 4/1980 Peter ................................. 73/204

Primary Examiner—Jerry W. Myracle
Attorney, Agent, or Firm—Edwin E. Greigg

[57] ABSTRACT

An apparatus is proposed for burnoff of deposits from at least hot wire and/or hot film resistors in the air flow rate measurement circuit of an internal combustion engine, wherein during the burnoff procedure a separate electric current circuit is furnished to provide for the resistors to be burned off with high electric currents. In one embodiment, the resistors to be burned off are placed in a separate current path between two operational voltage leads, while in another embodiment, that there is provided a parallel circuit arrangement of individual resistors to be burned off, whereupon the total electric current flow through the individual resistors is then seprately controlled in closed-loop fashion.

11 Claims, 2 Drawing Figures

APPARATUS FOR BURNOFF OF A RESISTOR, IN PARTICULAR OF A HOT WIRE IN AN AIR FLOW RATE METER OF AN INTERNAL COMBUSTION ENGINE

BACKGROUND OF THE INVENTION

The present invention relates to apparatus for burnoff of hot wire resistors in an air flow rate meter used in an internal combustion chamber.

When hot wires or hot films are used in air flow rate meters in internal combustion engines, then from time to time a burnoff or glow-heating of this resistor element must be undertaken so as to burn off or forcefully remove dirt particles deposited thereon. This must be done because of the necessity for attaining measurement results which are as free of error as possible over a long period of operation. It is already known to dispose an air flow rate meter in an internal combustion engine, having a bridge circuit and a hot wire as a measuring resistor; the hot wire is held to a constant temperature by means of a control device for the electric current which precedes the bridge circuit and is burned off after the end of each operational cycle on the basis of a predefined bridge imbalance. Generally, a further resistor in the measurement bridge is associated with the hot wire in the air intake of the engine, in order to compensate for the effect of the aspirated air temperature on the measurement result.

It has proved to be desirable for this compensating resistor, as well, to be burned free of soil, at least occasionally, so that its effectiveness is maintained.

OBJECT AND SUMMARY OF THE INVENTION

With the apparatus according to the invention there is provided resistance means for burnoff of a hot wire or hot film in the air flow rate meter consisting of a bridge resistance network in circuit with an electric current control device, the resulting improvement providing an extremely effective burnoff of the resistors, or of the hot wire or wires, located in the burnoff circuit. This is because the normal circuitry of the hot wire is disconnected and a separate burnoff circuit is provided. Depending on the realization of the burnoff circuit, the electric current control device in series with the bridge circuit can be dimensioned as substantially weaker, and thus more cost-favorable, than in the known arrangement.

The proposed arrangement is particularly advantageous when the bridge circuit includes a plurality of hot wires; then, for instance, a single hot wire can perform the air flow measurement and a series circuit of at least two corresponding hot wires serves to compensate for the aspirated air temperature. Not only has a series circuit of hot wires proved favorable, but a parallel circuit has proved favorable as well.

The invention will be better understood and further objects and advantages thereof will become more apparent from the ensuing detailed description of preferred embodiments taken in conjunction with the drawings.

DETAILED DESCRIPTION OF THE PREFERRED EMBODIMENTS

Figure 1:
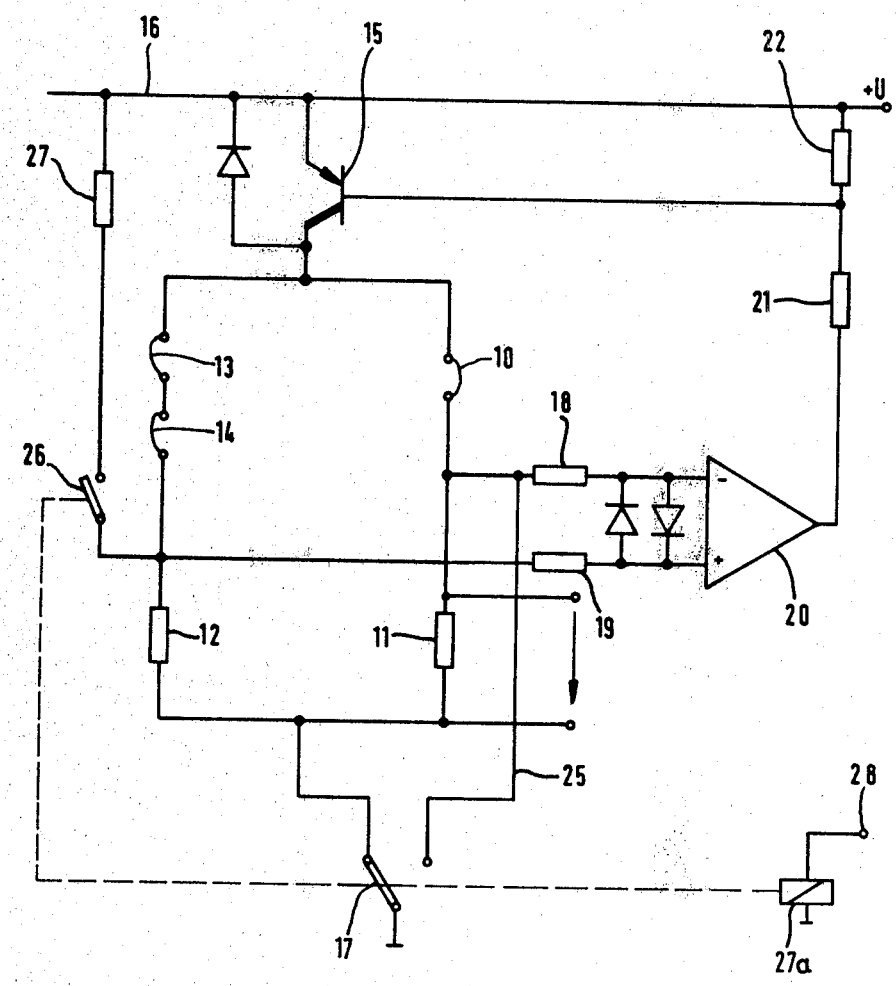
FIG. 1 shows an electrical schematic diagram of a first preferred embodiment of a burnoff apparatus according to the invention.
Figure 2:
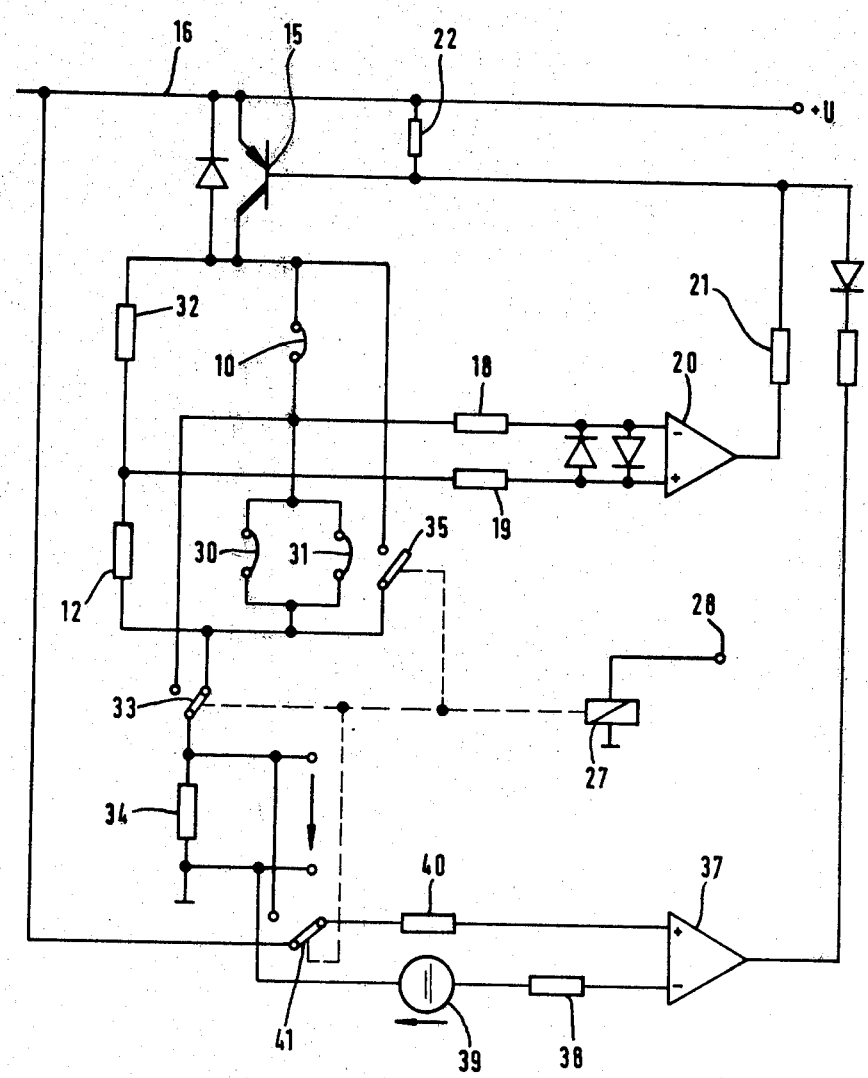
FIG. 2 shows an electrical schematic diagram of a second and further preferred embodiment of the burnoff apparatus.

Referring now to the drawings, FIGS. 1 and 2 each show an air flow rate measurement circuit in an internal combustion engine. In FIG. 1, a hot wire 10 forms one bridge branch of a measurement bridge having two resistors 11 and 12 as well as of a series circuit of two further hot wires 13 and 14. The bridge circuit is linked via a transistor 15, as the electric current control device, with the positive lead 16 of a battery voltage source, not shown, and is connected on the opposite side via a switch 17 to ground. The air flow rate signal can be picked up as a voltage drop over the bridge resistor 11 and then processed further. From diagonal points of the bridge, each of the resistors 18 and 19 leads to one of two inputs of a differential amplifier 20, which is linked on the output side, via a resistor 21, with the base of the transistor 15. This base is in addition further coupled, via a resistor 22, with the positive lead 16.

The switch 17 is embodied as an alternating switch and in its second position it connects a lead 25, which is connected at the junction point of the hot wire 10 and the resistor 11, to ground. A further switch 26 is located in series with a resistor 27 between the junction point of the resistor 12 and the hot wire 14 and the positive lead 16, and in the normal case, the switch 26 is opened. Both switches 17 and 26 are controllable by means of a relay 27a on the basis of a signal on terminal 28 for a burnoff signal.

In the illustrated switch positions, the circuit arrangement shown here functions as an air flow rate meter. If the relay 27a is energized, and the alternating switch 17 is thereby moved into its second position and the switch 26 is closed, then a separate electrical current circuit is formed, from the positive lead 16, via the resistor 27, the switch 26, the two hot wires 13 and 14 serving to compensate for the aspirated air temperature, the primary hot wire 10 and the switch 17, to ground. With an appropriately selected dimensioning of the resistor 27, a desired burnoff current then flows through the individual hot wires 10, 13 and 14. Depending on the overall dimensions of the resistors 18 and 19 as well, the differential amplifier 20 then emits a signal at its output side which blocks the transistor 15.

To prevent mechanical stress on the individual hot wires, it is efficient to wait to perform the burnoff procedure until such time as the air throughput in the air intake of the engine has come to a stop. This waiting period also has a favorable effect in terms of reducing the required power supply.

Depending on the type of embodiment, the resistor 27 can also be replaced by a source of electric current, or it can be included additionally in the electric lead, so that the burnoff procedures will take place with a predefined and adjustable electric current.

While in the subject of FIG. 1 the individual hot wires are switched into a separate electric current circuit during the burnoff, in the burnoff apparatus of FIG. 2 only the bridge circuit is disconnected and the increased electric current then required is furnished via the electric current control device 15.

Identical components in identical positions are provided in FIGS. 1 and 2 with the same reference numerals.

In the arrangement of FIG. 2, a parallel circuit of two hot wires 30 and 31 is located in series with the hot wire 10, so that one of the two bridge branches is made up entirely of hot wires as the resistors. In the second bridge branch, there is a resistor 32, which is in series with the resistor 12. The terminal of the measurement bridge on the ground side is carried to a switch 33 and subsequently to a measuring resistor 34. The switch 33 is embodied as an alternating switch and its second triggerable contact is linked with the junction point of the hot wires 10 and 30 and 31. A further switch 35, in the closed position, connects the two terminals on the operational voltage side of the measurement bridge, so that all the hot wires are switched in parallel. During the measurement operation, the air flow rate signal can be picked up at the measuring resistor 34. During the burnoff, this voltage signal serves to control the electric current control device 15 via a separate differential amplifier 37. While a constant potential is available at the negative input of this differential amplifier 37 via a resistor 38 from a voltage source 39, the positive input is connected, via a resistor 40 and an alternating switch 41, selectively with the positive lead 16 or with the junction point of the alternating switch 33 and the measuring resistor 34. All three switches 33, 35 and 41 are switched on the basis of a burnoff relay 27 which receives a corresponding trigger signal from the terminal point 28.

In FIG. 2, the individual switch positions are shown during measurement operation. In other words, in accordance with the bridge imbalance the electric current control device 15 is triggered via the differential amplifier 20 and the air flow rate signal can be picked up at the resistor 34. The voltage source 39 preceding the negative input of the differential amplifier 37 is so dimensioned that during the measurement operation the output signal of the amplifier 37 has no influence on the triggering of the transistor 15. If the individual hot wires are to be burned off, which is most advantageous when the air in the air intake tube is calm, then the individual switches are each directed into their other positions on the basis of a trigger signal at the terminal point 28. As a result of this, the individual resistors or hot wires 12, 32, 10, 30 and 31 are switched in parallel and the total electric current through these individual resistors can be controlled in closed-loop fashion on the basis of the voltage drop at the measuring resistor 34 and of the output signal of the differential amplifier 37.

The primary advantage of the subject of FIG. 2 is that the burnoff procedure occurs with an electric current which can be regulated, and accordingly takes place with precisely defined dimensions.

Which of the two arrangements shown in FIGS. 1 and 2 is actually put to use depends on which is the most efficient arrangement from the standpoint of aspirated air temperature compensation. Furthermore, the design of the transistor 15 acting as the electric current control device should be evaluated as a criterion in making this decision, as should be the fact that the arrangement of FIG. 2 has, in the measuring resistor 34, an additional resistor which must furthermore be dimensioned with a high power requirement.

The compensating resistors for compensation of the aspirated air temperature are embodied as a series or parallel circuit of hot wires in order to be able to attain this object with as few different components as possible for the sake of mass production of hot wire air flow rate meters.

It will be appreciated that semiconductor components can naturally also be used in place of the illustrated mechanical switches.

What is essential in the subjects of both figures is that the electric current circuits existing during the measurement operation are disconnected from the individual hot wires, and an independent electric current circuit is set up with the appropriate hot wires for the purpose of and at the time of the burnoff procedure.

The foregoing relates to preferred exemplary embodiments of the invention, it being understood that other embodiments and variants thereof are possible within the spirit and scope of the invention, the latter being defined by the appended claims.

What is claimed and desired to be secured by Letters Patent of the United States is:

1. An apparatus for burnoff of deposits from at least two resistors of an air flow rate measurement circuit for an internal combustion engine, in which the at least two resistors are normally connected in a parallel arrangement in a first electric current circuit controlled by an electric current control device during a measurement operation, wherein the apparatus comprises:
   a second electric current circuit which is different from the first electric current circuit; and
   switch means for switching the at least two resistors in a series arrangement into the second electric current circuit during a burnoff operation.

2. An apparatus, described in claim 1, wherein:
   the air flow rate measurement circuit comprises a bridge circuit having two inputs and two parallel current paths extending between the two inputs, each parallel current path including a diagonal point and two resistive current paths or branches extending between the diagonal point and the two inputs, respectively, each of the two bridge branches connected between one of the bridge inputs and the two bridge diagonal points, respectively, including at least one resistor of the at least two resistors to be burned off;
   the second electric circuit includes two operational voltage lines; and
   the switch means comprises means for coupling the two bridge diagonal points to the two operational voltage lines, respectively, during the burnoff operation.

3. An apparatus for burnoff of deposits from at least two resistors of an airflow rate measurement circuit for an internal combustion engine, in which the at least two resistors are normally connected in a series arrangement in a first electric current circuit controlled by an electric current control device during a measurement operation, wherein the apparatus comprises:
   a second electric current circuit which is different from the first electric current circuit; and
   switch means for switching the at least two resistors in a parallel arrangement into the second electric current circuit during a burnoff operation.

4. An apparatus, as described in claim 3 wherein:
   the air flow rate measurement circuit comprises a bridge circuit which includes two inputs, and two parallel current paths connected between the two inputs, each parallel current path including a diagonal point and two resistive paths, or branches extended between the diagonal point and the two bridge inputs, respectively, each of the two bridge branches extending from one bridge diagonal point to the two bridge inputs, respectively, including at least one resistor of the at least two resistors to be burned off;

the second electric current circuit includes two operational voltage lines; and the switch means includes a first switching means for disconnecting the bridge circuit from the first electric current circuit, second switching means for connecting the two bridge inputs, and third switching means for connecting the two bridge inputs to one operational voltage line and the one bridge diagonal point to the other operational voltage line, during the burnoff operation.

5. An apparatus, as described in claims 2 or 4, wherein the second electric current circuit comprises:

a measurement resistor which is connected in series with the bridge circuit during the burnoff operation; and a closed-loop electric current control means for controlling the flow of electric current through the resistors to be burned off during the burnoff operation in accordance with the voltage drop across the measuring resistor.

6. An apparatus, as described in claim 1 or 3, wherein the second electric current circuit comprises electric current control means for controlling the flow of electric current through the resistors to be burned off in an open-looped fashion during the burnoff operation.

7. An apparatus, as described in claim 1 or 3, wherein the second electric current circuit comprises electric current control means for controlling the flow of electric current through the resistors to be burned off in a closed-loop fashion during the burn off operation.

8. An apparatus, as described in claims 1 or 3, which further comprises an electric current source for supplying current to the first and second electric current circuits.

9. An apparatus as described in claim 1 or 3, which further comprises:

a first electric current source for supplying current to the first electric current circuit; and a second electric current source for supplying power to the second electric current circuit.

10. An apparatus, as described in claim 1 or 3, wherein the resistors to be burned off are hot wire type resistors.

11. An apparatus, as described in claim 1 or 3, wherein the resistors to be burned off are hot film type resistors.

* * * * *